US00PP35813P2

(12) United States Plant Patent
Peil

(10) Patent No.: US PP35,813 P2
(45) Date of Patent: May 21, 2024

(54) APPLE TREE NAMED 'Pia41'

(50) Latin Name: *Malus domestica*
Varietal Denomination: Pia41

(71) Applicant: Julius Kühn-Institut (JKI), Federal Research Centre for Cultured Plants, Quedlinburg (DE)

(72) Inventor: Andreas Peil, Dresden (DE)

(73) Assignee: Julius Kuhn-Institut (JKI), Federal Research Centre for Cultivated Plants, Quedlinburg (DE)

( * ) Notice: Subject to any disclaimer, the term of this patent is extended or adjusted under 35 U.S.C. 154(b) by 0 days.

(21) Appl. No.: 18/237,101

(22) Filed: Aug. 23, 2023

(51) Int. Cl.
*A01H 5/08* (2018.01)
*A01H 6/74* (2018.01)

(52) U.S. Cl.
USPC ..... Plt./172

(58) Field of Classification Search
USPC ..... Plt./161, 172
CPC ..... A01H 5/08; A01H 5/00; A01H 6/7418; A01H 6/74
See application file for complete search history.

(56) References Cited

PUBLICATIONS

AFG Apple Day 2023 retrieved on Nov. 8, 2023 at https://www.agf.nl/photos/album/10490/appeldag-2023/, 2 pp. (Year: 2023).*
Deltaplan Agrarisch Waterbeheer 2023 retrieved on Nov. 8, 2023 at https://agrarischwaterbeheer.nl/content/fotoreportage-d%C3%A9-appeldag-2023, 2 pp. (Year: 2023).*

* cited by examiner

*Primary Examiner* — June Hwu
(74) *Attorney, Agent, or Firm* — The Webb Law Firm

(57) ABSTRACT

A new and distinct *Malus domestica* variety is provided that produces large apples having a light green fruit skin color, desirable eating characteristics, and long keeping duration.

7 Drawing Sheets

Botanical classification: *Malus domestica.*
Varietal denomination: 'Pia41'.

BACKGROUND OF THE INVENTION

The present invention comprises a new and distinct variety of apple tree, botanically known as *Malus domestica*, and referred to by the varietal name 'Pia41'. The new variety was discovered and first asexually reproduced by grafting in 2010 in Dresden-Pillnitz, Germany. The new variety is the result of a cross of an unnamed and unpatented *Malus domestica* variety as the male parent with 'Honeycrisp', a *Malus Mill.* variety (female parent, U.S. Plant Pat. No. 7,197). Comparisons to the male parent cannot be made, as the male parent is no longer available. However, the new variety differs from 'Honeycrisp' in having a more flat shape and light green skin color (with no over color). When compared to a standard 'Granny Smith' apple variety (unpatented), 'Pia41' exhibits a similar green color in general, but 'Pia41' differs in fruit shape (more flat) and the skin is light green in color that turns yellow when overripe.

The new variety has not been evaluated under all possible environmental conditions. The phenotype may vary with variations in environment without a change in the genotype of the plant. The new variety has been trial and field tested and has been found to retain its distinctive characteristics and remain true to type through successive asexual propagations.

DESCRIPTION OF THE DRAWINGS

The accompanying photographic drawings illustrate the new variety at 8 years of age, with the color being as nearly true as is possible with color illustrations of this type.

DESCRIPTION OF THE PLANT

Figure 1:
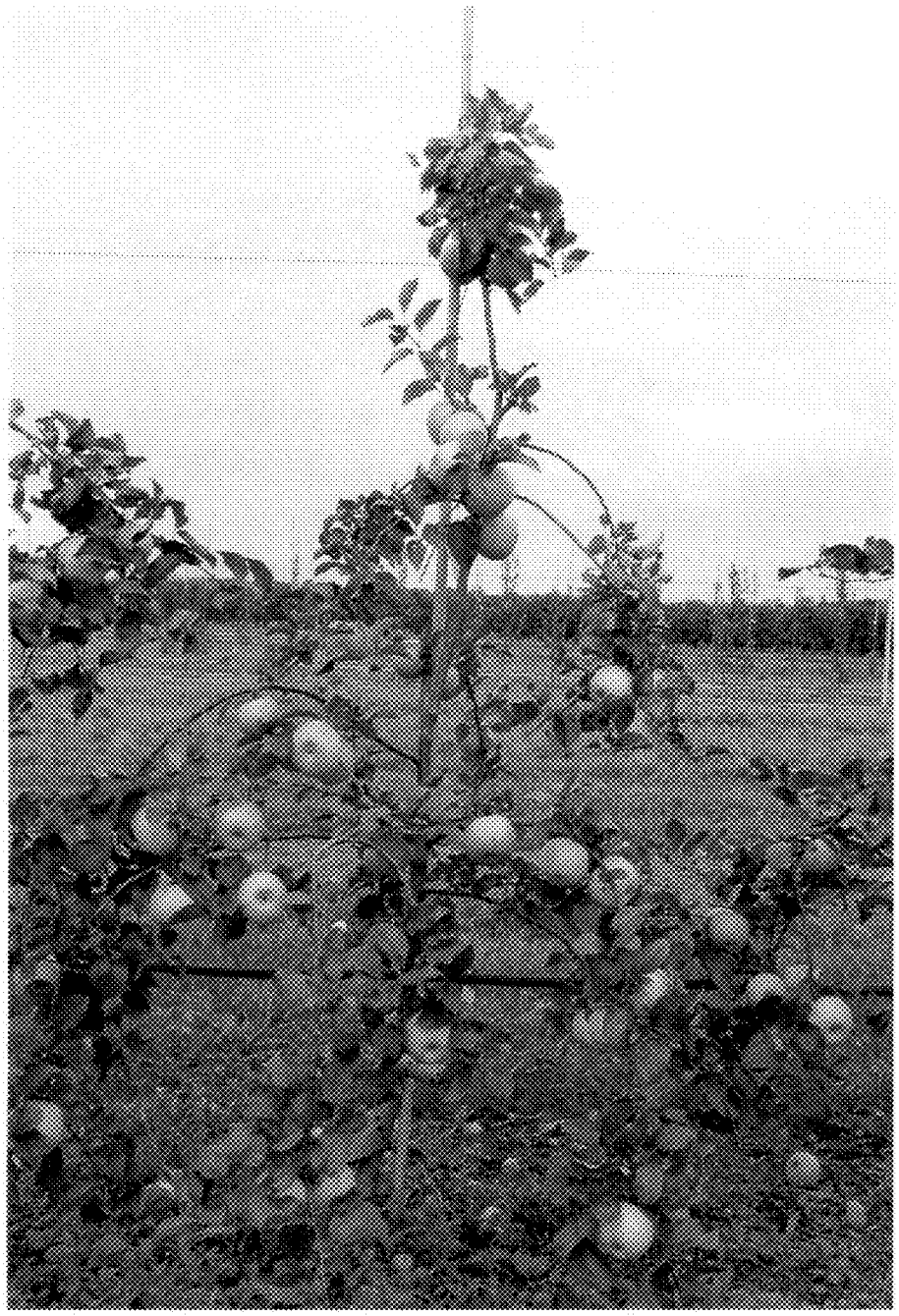
FIG. 1 is an image of a fruiting tree of the new variety.
Figure 2:
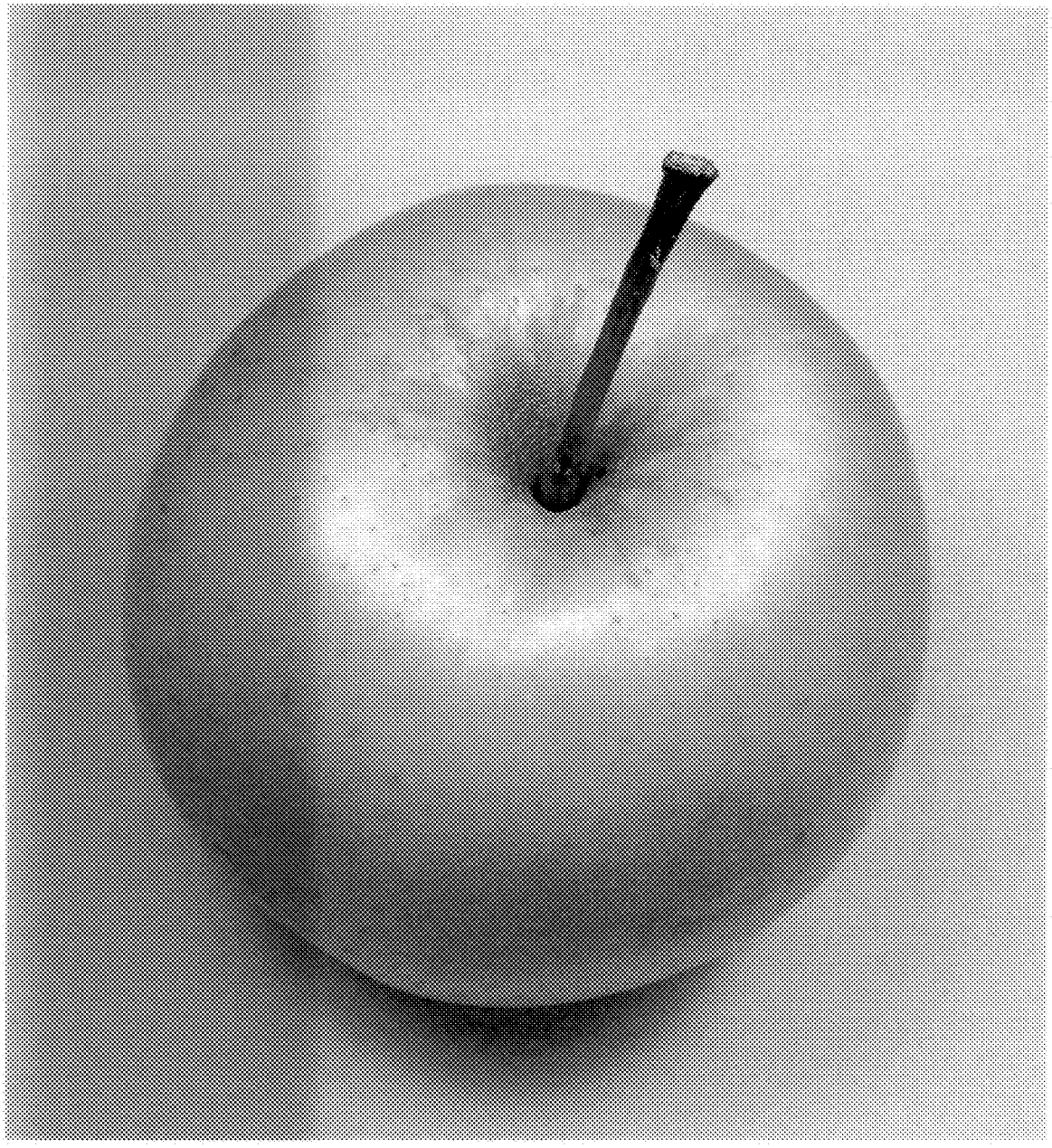
FIG. 2 is an image of a fruit of the new variety.
Figure 3:
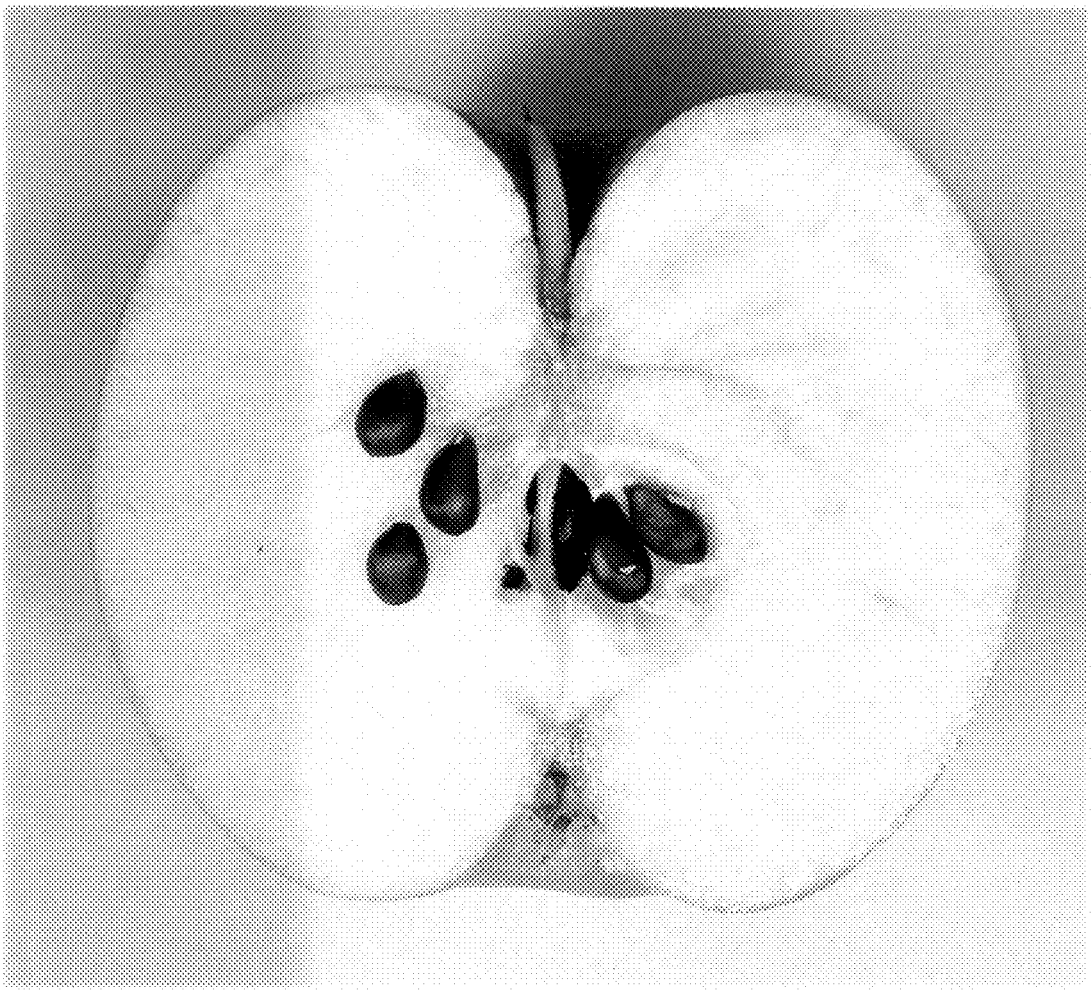
FIG. 3 is an image of a fruit of the new variety in longitudinal section.
Figure 4:
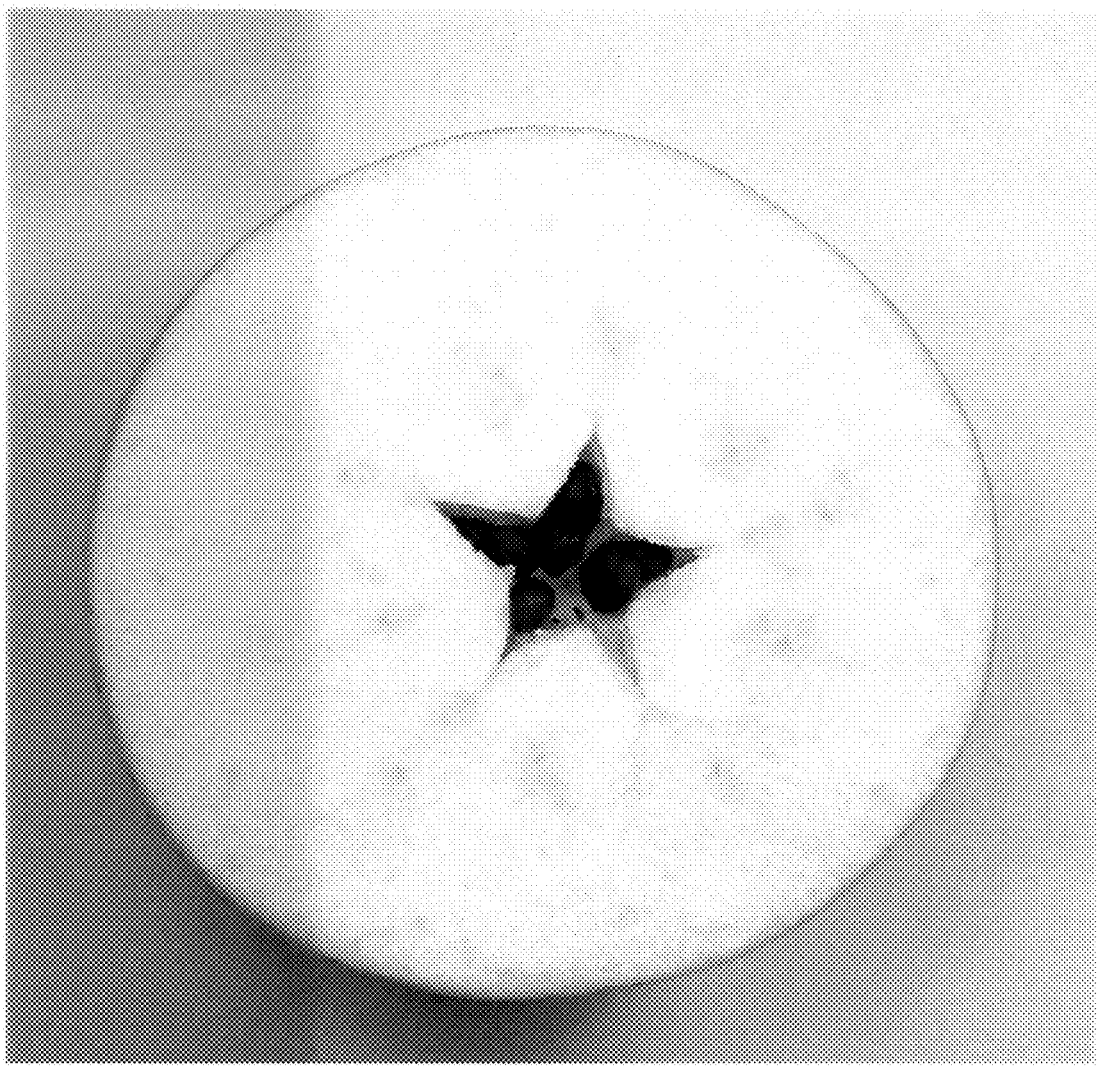
FIG. 4 is an image of a fruit of the new variety in transverse section.
Figure 5:
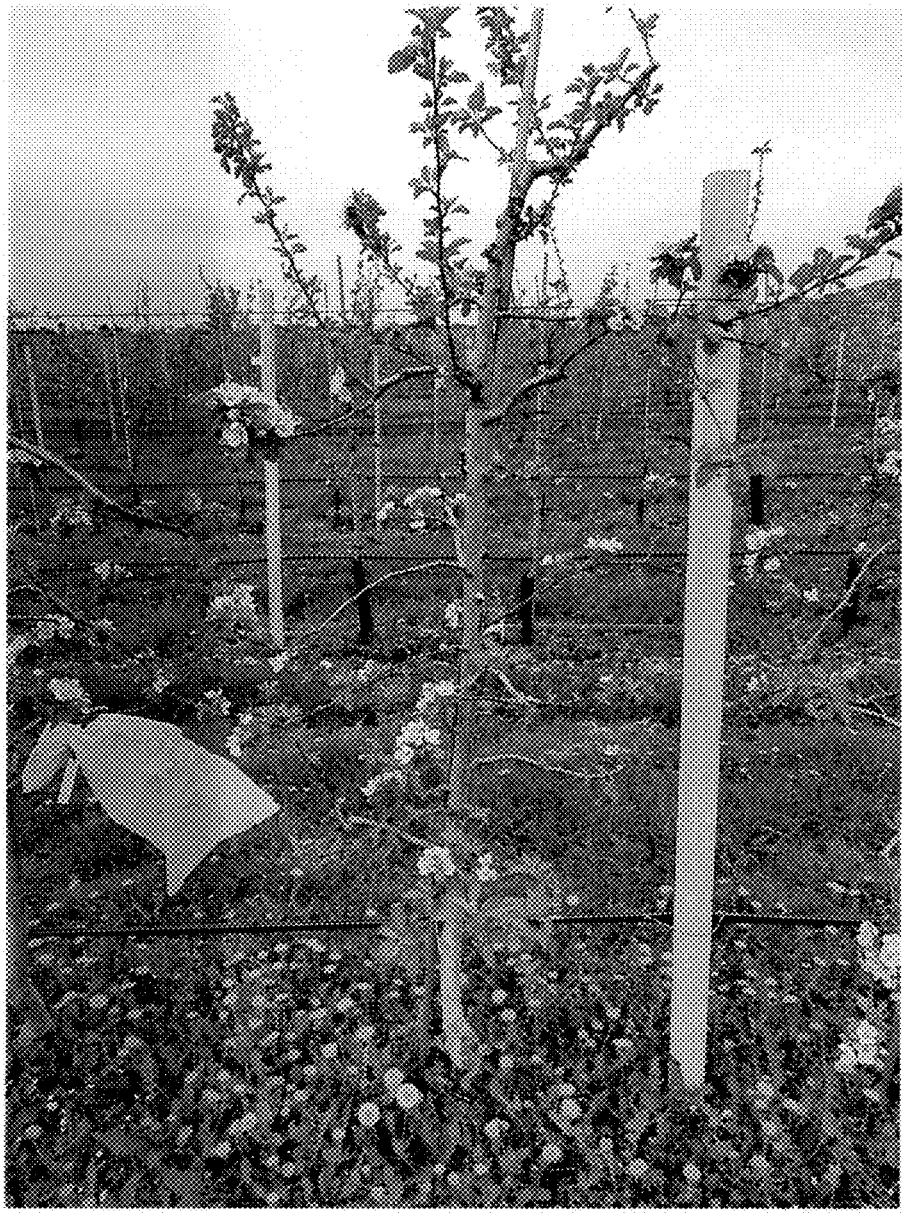
FIG. 5 is an image of a flowering tree of the new variety.
Figure 6:
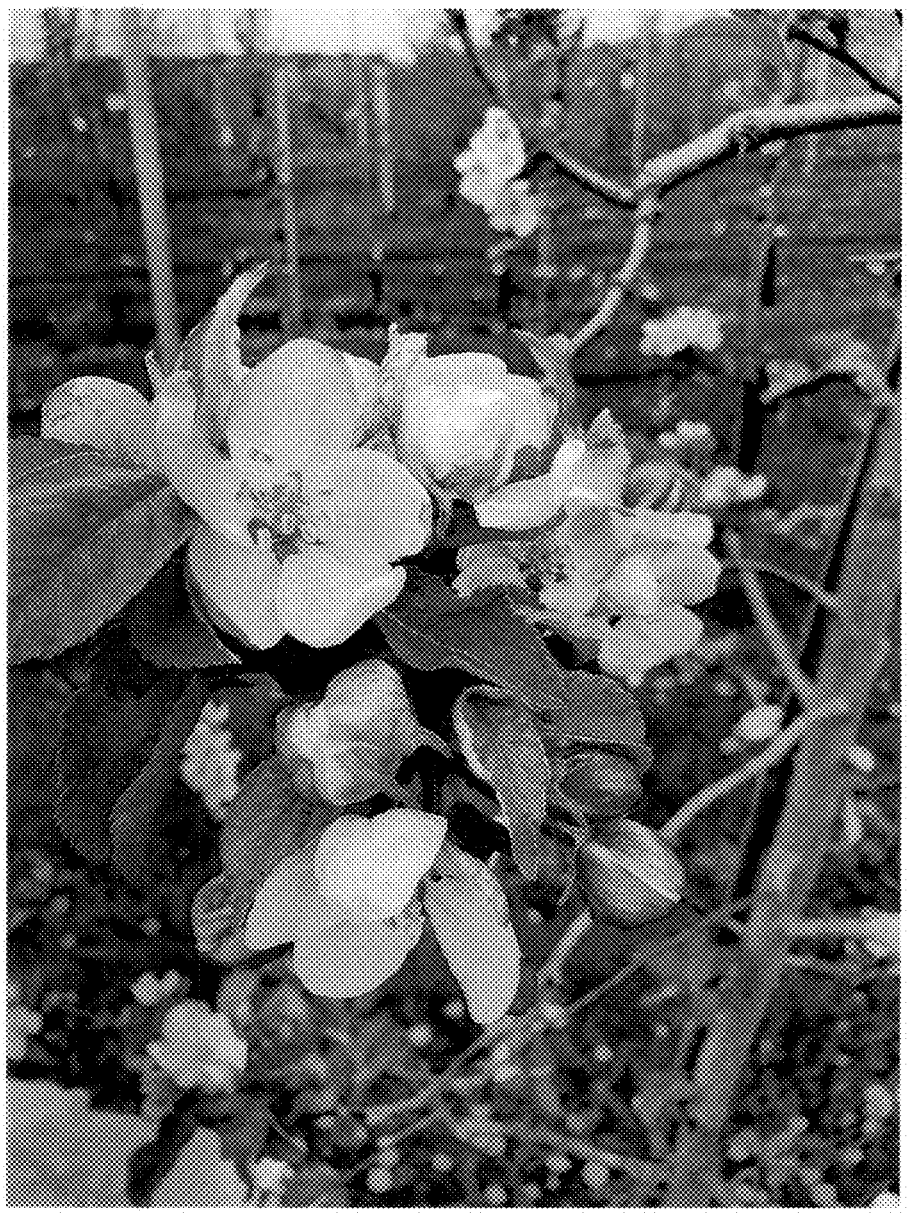
FIG. 6 is an image of the flowers of the new variety.
Figure 7:
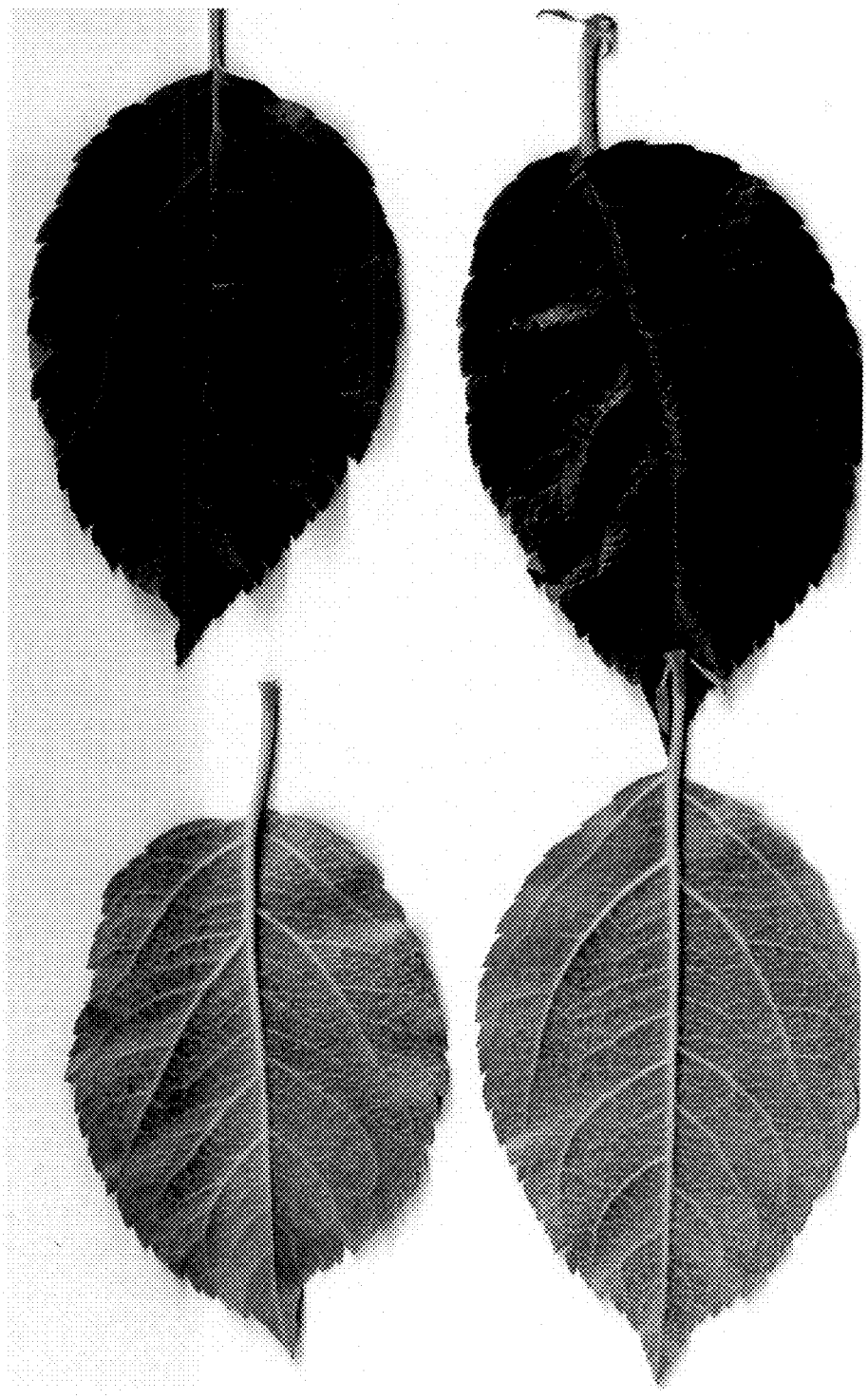
FIG. 7 is an image of the leaves of the new variety.

The following detailed description sets forth the characteristics of the new variety at 8 years of age. The new variety was grown in an open field under standard apple orchard conditions in Dresden-Pillnitz, Germany. The color readings were taken under artificial light for the leaves and flowers and in natural daylight for the remainder. Color references are primarily to RAL 840-HR Colour Cards and Royal Horticultural Society (RHS) Colour Chart 2007, fifth edition, except where ordinary color terms are used.

TREE

Height: 2.5 m.
Average spread: 151.0 cm.
Vigor: Medium.
Form: Upright.
Growth type: Ramified.
Bearing: On long and short shoots.
Trunk:
*Height.*—0.6 m.
*Diameter.*—4.9 cm, measured at 65.0 cm above the soil level.

*Bark color.*—RAL7034.
*Lenticels.*—Color: RAL9001. Density: High.
Branches:
*Form.*—Rounded.
*Diameter.*—Average of 16.4 mm.
*Color.*—RAL8008.
*Surface texture.*—Rough.
*Average angle.*—74°.
*Lenticels.*—Shape: Oblong. Density: High. Color: RAL1001.
Leaves:
Length: Average of 8.5 cm.
Width: Average of 5.3 cm.
Shape: Obtuse.
Apex: Acuminate.
Base: Rounded.
Margin: Senate type 2 per the UPOV International Protection of New Varieties of Plants — Apple.
Pubescence:
*Upper surface.*—Absent.
*Lower surface.*—Medium.
Color:
*Young leaves.*—Upper surface: RAL6025. Lower surface: RAL6021.
*Mature leaves.*—Upper surface: RAL6002. Lower surface: RAL6011.
Petiole:
*Length.*—Average of 2.1 cm.
Veins:
*Type.*—Pinnate, intensified on the lower surface.

FLOWERS

Blooming time: Medium to late in Dresden-Pillnitz, Germany.
Number of flowers per cluster: 6-7.
Pollinator required: Yes.
Buds:
*Length.*—14.0 mm.
*Width.*—15.0 mm.
*Color.*—RAL3018.
Pedicels:
*Length.*—17.0-19.0 mm.
*Diameter.*—1.3-1.5 mm.
*Color.*—RAL6003.
Petals:
*Number per flower.*—5.
*Length.*—16.0-19.0 mm.
*Width.*—14.0-16.0 mm.
*Shape.*—Ovoid.
*Margin.*—Smooth.
*Color.*—When opening: Lower surface: Dark pink. Fully opened: Upper surface: White to light pink. Lower surface: Dark pink.
Sepals:
*Length.*—6.0-7.0 mm.
*Width.*—4.5 mm.
*Shape.*—Triangular.
*Upper surface color.*—RAL1013.
*Lower surface color.*—RAL3015.
Stamens:
*Number (per flower).*—20.
*Filament length.*—7.0 mm.
Anthers:
*Shape.*—Double cylinder.
*Length.*—2.5 mm.
*Color.*—RAL1016.
Pistils:
*Length.*—15.0-16.0 mm.
Style:
*Length.*—9.0-11.0 mm.

FRUIT

Fruit:
*Maturity when described.*—Four weeks after harvest with fruits from cold storage.
*Average maturity/picking date.*—Late September in Dresden-Pillnitz, Germany.
*Form.*—Obloid.
*Size.*—Axial diameter: Tall, 55.0-75.0 mm. Transverse diameter: Large to very large, at least 70.0-90.0 mm.
*Cavity.*—Depth: Deep. Breadth: Broad, russeted.
*Basin.*—Depth: Deep. Width: Broad.
*Calyx.*—Closed.
Skin:
*Thickness.*—Thin and easy to penetrate.
*Texture.*—Easy to bite.
*Tendency to crack.*—No.
*Color.*—RHS 154B that changes to yellow when harvested too late with few small dots present and no over color.
Flesh:
*Aroma.*—Mild and pleasant.
*Color.*—RHS 8D with light striation of RHS 1C.
*Texture.*—Firm, crispy, and juicy.
*Eating quality.*—Very good with a balanced sweetness.
Core:
*Bundle area.*—Broad.
*Calyx tube.*—Conic.
*Axillary cavity.*—Heart shaped, open.
Seeds:
*Number perfect.*—10.
*Number in one cell.*—2.
Stem:
*Length.*—Approximately 23.0 mm.
*Width.*—2.5 mm.
*Color.*—RHS 175C at stem attachment and RHS 200B towards the top.
Russet area size:
*Around the fruit eye basin.*—Up to small.
*Around the fruit stalk attachment.*—Up to medium.
Use: Fresh fruit consumption.
Keeping quality: Very good-retains quality, texture, firmness, and juiciness for up to six months in cold storage at 3° C.
Disease resistance: Scab resistance to distinct scab strains with only slight symptoms possible. Exhibits decreased susceptibility to powdery mildew.

I claim:

1. A new and distinct variety of apple tree named 'Pia41', as is herein illustrated and described.

* * * * *